United States Patent [19]

Siposs

[11] 4,336,224
[45] Jun. 22, 1982

[54] BUBBLE OXYGENATOR

[75] Inventor: George G. Siposs, Costa Mesa, Calif.

[73] Assignee: Travenol Laboratories, Inc., Deerfield, Ill.

[21] Appl. No.: 122,779

[22] Filed: Feb. 19, 1980

Related U.S. Application Data

[63] Continuation of Ser. No. 3,994, Jan. 16, 1979, abandoned.

[51] Int. Cl.³ ............................................. A61M 1/03
[52] U.S. Cl. ...................................... 422/46; 422/47; 435/2
[58] Field of Search .................................. 422/46, 47; 261/DIG. 28; 128/DIG. 3; 195/1.8; 435/2

[56] References Cited

U.S. PATENT DOCUMENTS

| | | | |
|---|---|---|---|
| 2,887,107 | 5/1959 | Wehrli . | |
| 3,437,450 | 4/1969 | Greenwood . | |
| 3,578,411 | 5/1971 | Bentley et al. | 422/47 |
| 3,615,238 | 10/1971 | Bentley et al. | 422/46 |
| 3,898,045 | 8/1975 | Bailey | 422/46 |
| 3,994,689 | 11/1976 | DeWall . | |
| 4,058,369 | 11/1977 | Bentley et al. . | |
| 4,065,264 | 12/1977 | Lewin | 422/46 |
| 4,067,696 | 1/1978 | Curtis | 422/47 |
| 4,073,622 | 2/1978 | Luppi . | |
| 4,138,288 | 2/1979 | Lewin | 422/47 X |
| 4,138,464 | 2/1979 | Lewin | 422/47 X |
| 4,140,635 | 2/1979 | Esmond | 422/46 X |
| 4,180,896 | 1/1980 | Reed et al. | 422/46 X |
| 4,182,739 | 1/1980 | Curtis | 422/47 |
| 4,183,961 | 1/1980 | Curtis | 424/366 |
| 4,231,988 | 11/1980 | Kurata | 422/47 |
| 4,248,828 | 2/1981 | Bentley et al. | 422/47 |
| 4,268,476 | 5/1981 | Raible | 422/46 |
| 4,280,981 | 7/1981 | Harnsberger | 422/46 |
| 4,282,180 | 8/1981 | Raible | 422/46 |

FOREIGN PATENT DOCUMENTS 2315203  1/1977  France ................... 422/46

OTHER PUBLICATIONS

Shiley, "Model S-100 Oxygenator-Operating Instructions", Shiley Labs., 8-76.
Thoracic & Cardiovascular Surgery, vol. 76, No. 3, 9/78, inside front is piece and p. 1.

*Primary Examiner*—Barry S. Richman
*Attorney, Agent, or Firm*—Thomas R. Schuman; John A. Caruso; Paul C. Flattery

[57] ABSTRACT

The oxygenator is used for arterializing blood during open heart surgery. The oxygenator is factory-assembled and sterilized and is of economic and efficient design so that it can serve as a throwaway unit. Blood from the patient is oxygenated as it passes through the center of a tubular sparger with porous walls which supplies oxygen bubbles of the optimum size. The foaming blood is delivered to the top of the main oxygenator body where it is distributed by gravity flow downward across the heat exchanger tubing. The heat exchanger is wound as a flat coil with all connections outside of the oxygenator body. A silicone-coated sponge is located below the heat exchanger so that downwardly flowing foaming blood is defoamed as it passes through the sponge. Carbon dioxide and other gases are vented, and liquid blood gravitates into a tapered arterial reservoir.

58 Claims, 6 Drawing Figures

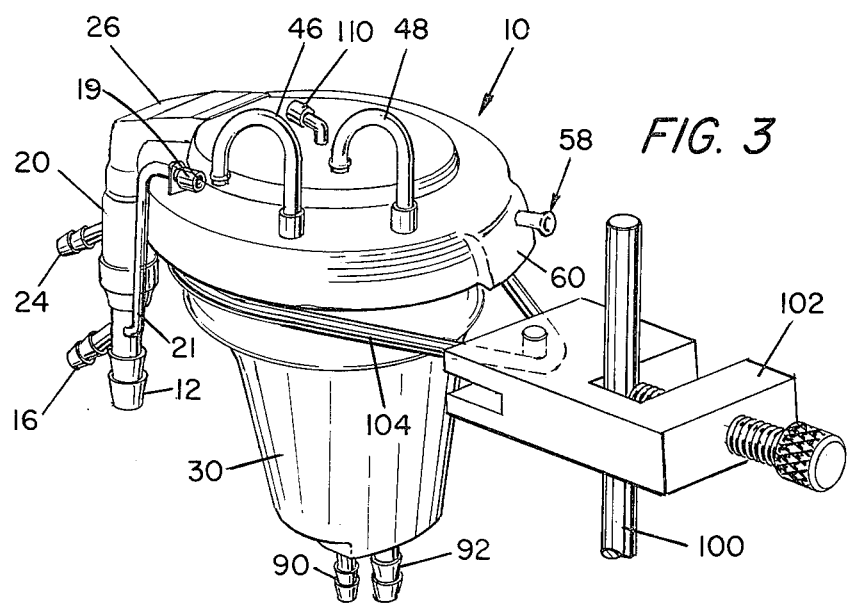
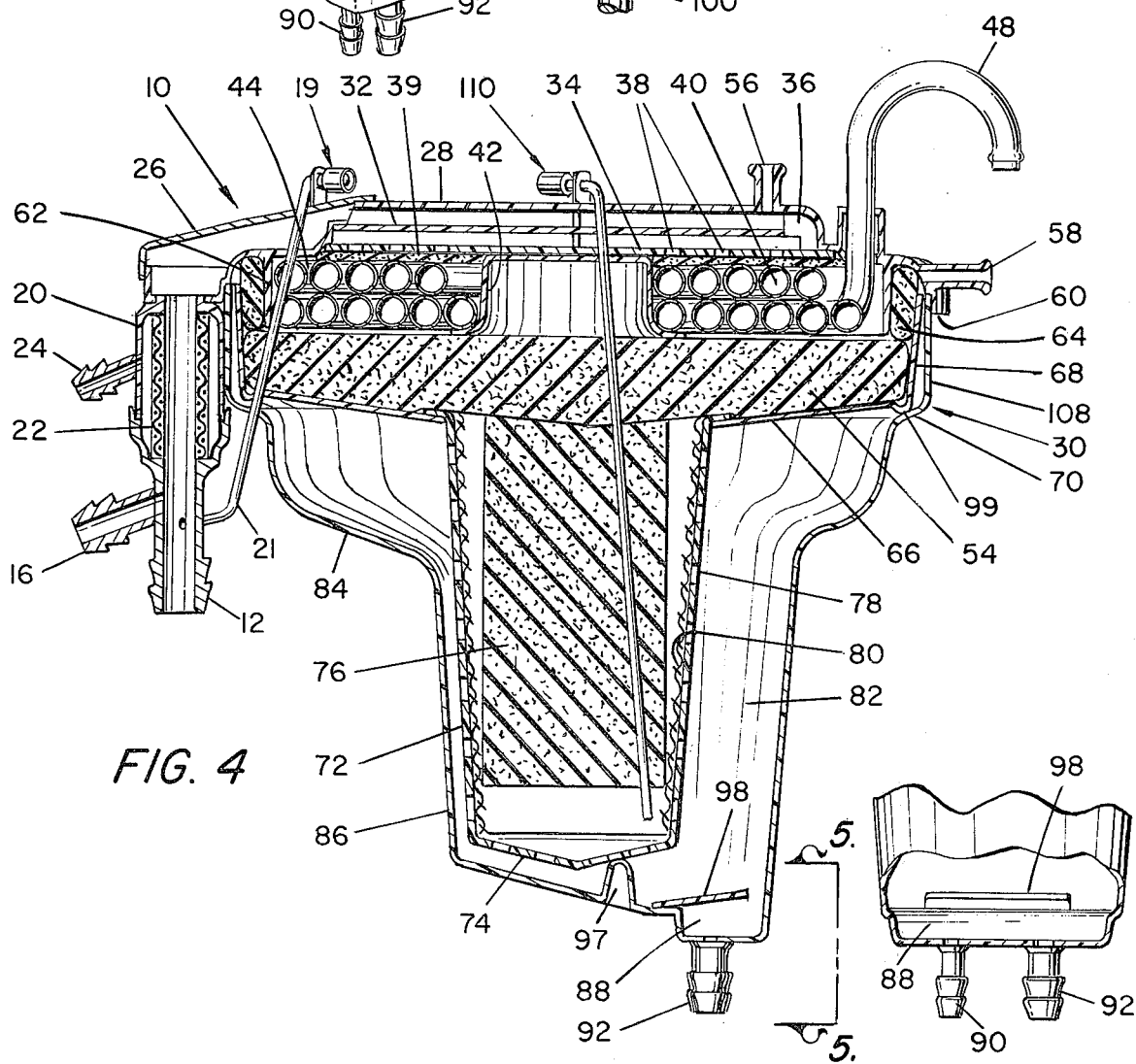
FIG. 3
FIG. 4
FIG. 5

BUBBLE OXYGENATOR

This is a continuation of application Ser. No. 3,994, filed Jan. 16, 1979, now abandoned.

BACKGROUND

This invention is directed to an oxygenator for oxygenating and temperature-controlling blood in extracorporeal circulation during surgery.

Extracorporeal circulation has been a routine procedure in the operating room for several years. An important component in the extracorporeal blood circuit is the blood oxygenator. The function of the oxygenator is to transfer oxygen into the venous blood so that the oxygen reacts with the hemoglobin with the resultant absorption of the oxygen and release of carbon dioxide. A historical survey of blood oxygenators was published in the Dec., 1961 issue of *Surgery*. The article was entitled "Theme and Variations of Blood Oxygenators," by R. A. DeWall, et. al.

Three principle types of blood oxygenators are known. In the membrane oxygenator, a semi-permeable membrane separates the blood from the oxygen, and gas exchange takes place by diffusion through the membrane. One type of membrane oxygenator is described in U.S. Pat. No. 3,413,095.

In the film oxygenator, a thin film of blood is exposed to an oxygen atmosphere. One type of film oxygenator is described in the Dec. 15, 1956 issue of *The Lancet*, page 1246, in an article entitled "Design of An Artificial Lung Using Polyvinyl Formal Sponge."

The bubble oxygenator introduces bubbles of oxygen directly into the blood. In the bubble oxygenator described in U.S. Pat. No. 3,578,411, the bubble chamber has a continuous convoluted path to promote the intermixing of the blood and the oxygen. U.S. Pat. No. 3,807,958 describes a bubble oxygenator which employs a plurality of vertical tubes through which the blood and oxygen mixture rises. U.S. Pat. No. 3,898,045 describes a bubble oxygenator having a lattice chamber tightly packed with spherical beads which are asserted to improve gas exchange. In a bubble oxygenator described in an article published in the Aug., 1957 issue of *Surgery*, which was entitled "Preliminary Studies On the Sponge-Oxygenator," by Adriano Bencini, et. al., a long multi-perforated needle is positioned in a cylindrical piece of polyurethane sponge. In U.S. Pat. No. 4,067,696, the rising flow of the blood and oxygen admixture passes through a three-dimensional open cell material which is asserted to aid in gas exchange on the hemoglobin.

SUMMARY

In order to aid in the understanding of this invention, it can be stated in essentially summary form that it is directed to a bubble oxygenator for use in an extracorporeal blood circuit wherein oxygen bubbles are delivered to the blood to cause foaming thereof, and the foaming blood is distributed over a heat exchanger whence it gravitationally descends and passes to a defoamer. Carbon dioxide is vented upward out of the defoamer, and liquid blood gravitates downward therefrom into an arterial blood reservoir.

It is thus an object of this invention to provide a bubble oxygenator which is a high performance unit and which offers significant clinical advantages, as well as conveniences to the user in a presterilized, low-cost, disposable unit. It is another object to provide a bubble oxygenator which has a substantially hard shell so that it can maintain structural shape, as well as provide good appearance and economic production methods by utilizing injection-molded synthetic polymer composition materials. It is another object to provide a blood oxygenator which is economic so that it can be disposable to eliminate the need for cleaning after use, to overcome the possibility of cross-contamination and to eliminate the cost of cleaning a unit. It is a further object to provide a factory-assembled blood oxygenator where assembly can be accomplished with appropriate jigs and fixtures to provide quality control in a "clean room" where the oxygenator can be assembled and later presterilized to be ready for use to thus overcome the clinical and economic problems of attempting to clean an oxygenator.

Other objects and advantages of the oxygenator of this invention will become apparent from a study of the following portion of the specification, the claims, and the attached drawings.

BRIEF DESCRIPTION OF THE DRAWINGS

FIG. 3 is an isometric view similar to FIG. 2, but showing the oxygenator mounted on a stand.

FIG. 4 is a section taken generally along the line 4—4 of FIG. 1, with parts broken away and parts taken in section.

FIG. 5 is a section taken generally along the line 5—5 of FIG. 4, with parts broken away.

DESCRIPTION OF THE PREFERRED EMBODIMENT

Figure 1:
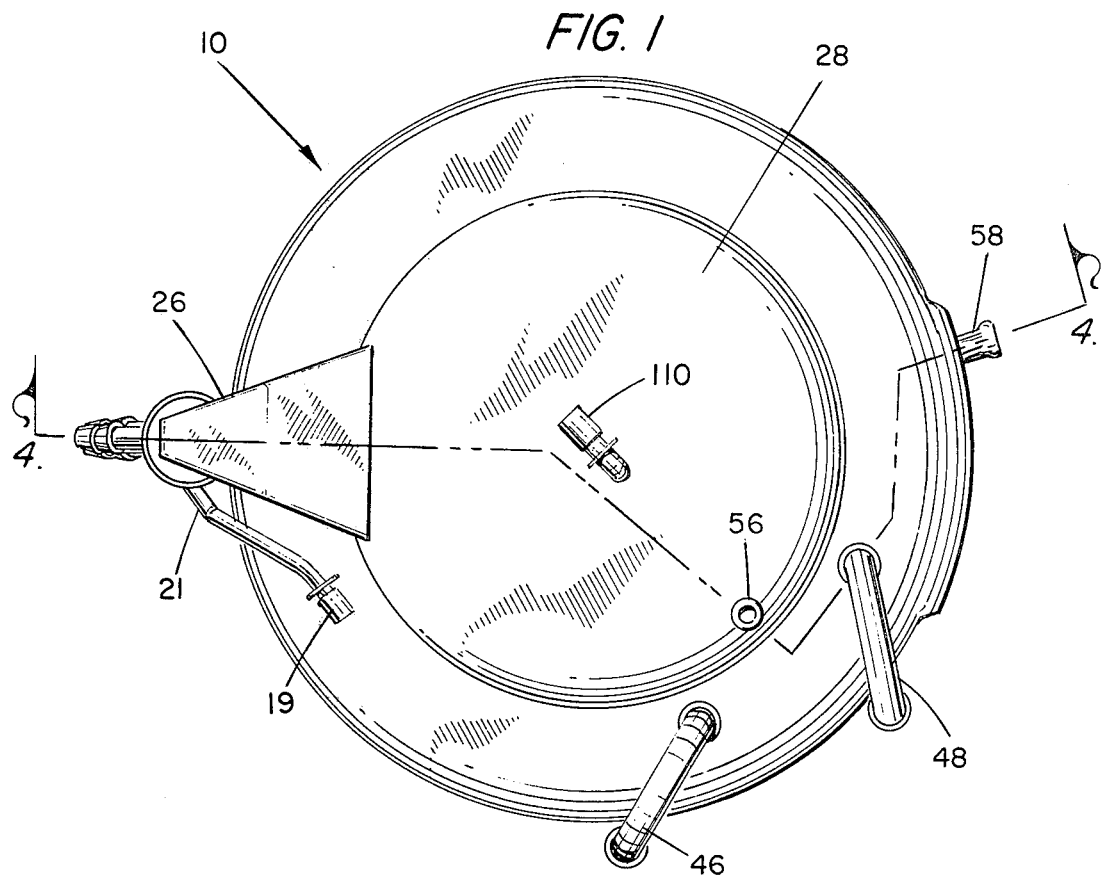
FIG. 1 is a plan view of the oxygenator of this invention.
Figure 2:
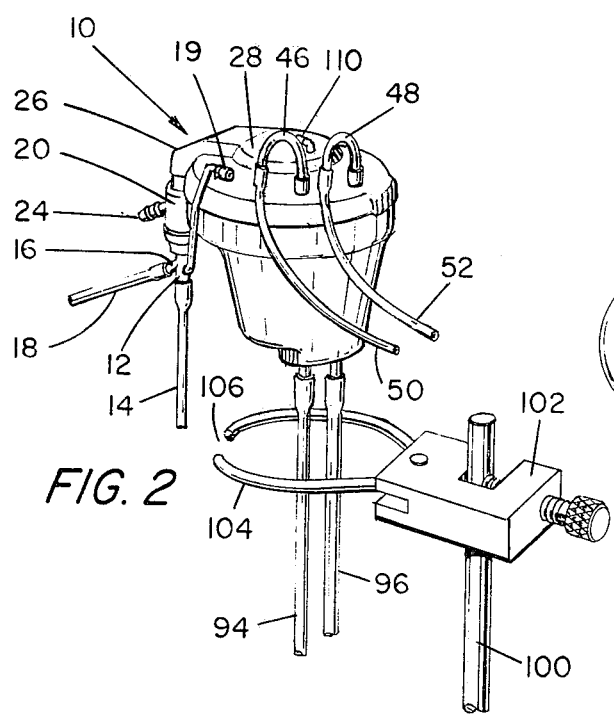
FIG. 2 is a perspective thereof on reduced scale showing the manner in which the oxygenator is connected to a system and is mounted.
Figure 6:
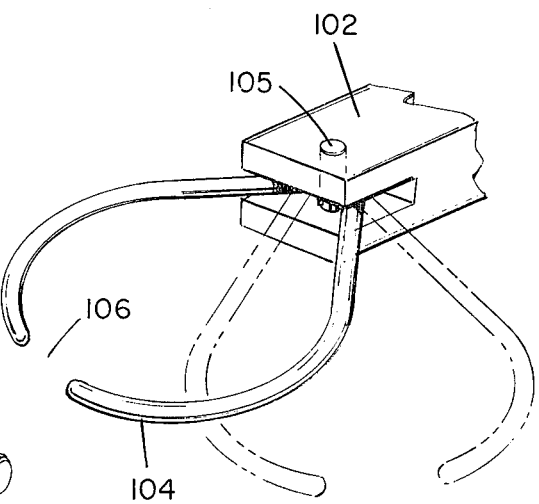
FIG. 6 is a detailed isometric view of the support clamp.

The preferred embodiment of the oxygenator of this invention is generally indicated at 10 in FIGS. 1 through 4. Oxygenator 10 is manufactured as a permanently assembled, low-cost, disposable unit which is principally made of injection-molded parts so as to produce a substantially rigid structure which can be presterilized. The use of injection-molded parts makes for high quality, reliable parts which can be inexpensively reproduced and assembled, and yet provided for the cleanliness and reproducibility which is important in such a structure.

In studying oxygenator 10 in structural and functional detail, it will be considered in the direction of blood flow therethrough. Venous blood inlet connection 12 is directed downwardly. This permits the venous connection tubing 14 (see FIG. 2) which is directly connected to a venous cannula in the patient to hang in a half loop which makes it impossible for gas bubbles from the oxygenator to escape back towards the patient. Side fitting 16 is also an inlet fitting and is for the connection of tubing 18 from a cardiotomy reservoir, if one is used. If no cardiotomy reservoir is used in the procedure, then tubing 18 is clamped. Sample port 19 is connected by line 21 to connector 12 to obtain venous blood sample. A Luer opening is provided for the sample syringe.

Sparger assembly 20, seen in sectional detail in FIG. 4, has a cylindrical tubular body within which is fitted sparger tube 22. An exterior, cylindrical, tubular space around the sparger tube is open for the receipt of oxygen from oxygen connector 24. The interior of sparger tube 22 has approximately the interior diameter of venous blood inlet 12. Sparger tube 22 is a porous sparger. The porosity of sparger tube 22 is critical because it determines the size of the bubbles emitted. A porosity in the range of 90 "TEGRAGLAS," as manufactured by 3M company, of Minneapolis, Minn., is proper, although another similar structure may be used. If the oxygen bubbles are too small, they oxygenate the blood but do not remove carbon dioxide. If the bubbles are too large, the opposite occurs with removal of carbon dioxide, but with inadequate oxygenation. With the porosity indicated, less than 1:1 gas-to-blood flow ratio produces the correct bubble size. A lesser oxygen flow produces smaller bubbles and more oxygenation and vice versa.

The tubular shape of the sparger tube ensures that the entire volume of oxygen is evenly mixed with blood in a non-traumatic fashion. Since the oxygen bubbles flow inward into the blood, the blood is virtually floated over the inner surface of the sparger tube.

The sparger tube 22 may be made of or coated with a hydrophobic material. This would prevent the outward flow of blood therethrough should the oxygen supply lose pressure. Furthermore, the outside of the sparger tube 22 may have coating thereon which serves as an anti-bacterial filter, to filter from the oxygen flow particles graded larger than 0.2 micron. The coating is a layer of paste which dries to a porous surface.

Some of the oxygenation and consequent carbon dioxide removal takes place in the initial bubbling phase as the blood foams in sparger tube 22 and as the foaming mass rises. The blood with the entrained oxygen bubbles (with oxygen-$CO_2$ exchange beginning) proceeds upwardly propelled by gas flow, buoyancy, and the venous inflow of blood. Manifold 26 guides the upward flowing, foaming blood into the top of dome 28 of the main body 30 of oxygenator 10. The dome 28 is part of the cover of the lower part of the body. Within dome 28, flat distributor plate 32 receives the foaming blood. The foaming blood proceeds horizontally across distributor plate 32. As the blood foam flows across flat distributor plate 32, it is visible because the cover of the dome is transparent. Thus, it is easy to inspect the blood to see that it becomes bright red (as compared to the dark red venous blood at the inlet) as the blood acquires oxygen. Should the inflow of venous flow be uneven (for example, the result of a suction that is too high), waves of foam can be seen traversing flat distributor plate 32. This serves as a good indicator to the perfusionist who will then reduce the inflow rate.

The path through which the blood foam travels is torturous, thus insuring total mixing and gas exchange. This makes it possible to use small amounts of oxygen per volume of blood. The low oxygen-to-blood ratios mean less agitation of the blood, and thus less trauma to the blood cells. The lower oxygen ratio also produces less foaming so that less defoaming is required, together with the reduced oxygen cost.

Flat distributor plate 32 is spaced about ¼ inch from the outside shell of dome 28, and thus the foaming blood is distributed around the edges where it descends by gravity onto perforated distributor plate 34. The flow space 36 around the edge of flat distributor plate 32 allows the blood foam to flow downward without allowing any large gas bubble accumulation. Perforations 38 may be circular holes or slots. The slots may be radially or angularly directed, or arranged in any distribution to evenly disburse the foam as it passes downward through the perforations 38.

A thin disc-shaped dispersing layer 39 of foam may be placed below distribution plate 34 and above heat exchanger 40. The foam is open-celled to permit blood flow therethrough. The layer 39 may be uncoated to act as a distributor to evenly distribute the blood foam over heat exchanger 40, but preferably the foam layer 39 is silicone-coated. The silicone coating starts the vapor-liquid separation from the blood foam. This improves liquid blood contact with the coils of heat exchanger 40 to improve heat exchange efficiency. This layer is not always necessary.

Heat exchanger 40 is a pair of pancake-wound flat coil heat exchanger coils. Cone 42 in the center of the coils is inserted to prevent the blood escaping through the center of coils without heat exchanging. The coils of heat exchanger 40 are wound in opposite spirals in the two pancakes and are wound onto a mandrel which produces the interior opening into which cone 42 is inserted. The heat exchanger coils have a small space between the pancake windings, such as small space 44 and, with the pancakes wound in opposite spirals, inevitably there are small spaces between the coils of the two pancakes. These spaces permit the downward flow of the blood foam between the coils, and yet with the small space, heat exchange is efficient.

The positioning of the coiled heat exchanger tubing is horizontal; the pancake position provides for slow, parallel blood flow on the surface of the coils and through the openings between the coils. This also results in less cell damage. The horizontal positioning of the heat exchanger is useful in producing a low overall structure and in maximizing the arterial reservoir volume. The coils may be silicone-coated to encourage wet blood flow directly on the heat exchange coils without the insulating effect of entrained gas bubbles which provide the foam.

Another design feature presented by the particular heat exchange structure is the fact that the point where the heat exchanger tubing enters and leaves the oxygenator shell is above the blood level line at its highest point. In this way, complex sealing structures are not required, and there is no blood loss at the tube juncture and the body. There are no tubing joints within the body 30 of the oxygenator, but both free ends of the heat exchanger tubing are brought out of the body. As is seen in FIGS. 1 through 4, the coil ends 46 and 48 are shaped to have downwardly directed connections. This permits the connection of water tubing, such as tubing 50 and 52 (see FIG. 2) by which the water circulation is established through the heat exchanger tubing. Without a joint in the tubing within the shell, there is no danger of water leakage into the blood. The downwardly directed water connections enable the water-filled, heavily loaded lines to drape naturally. Three-eighths or one-half inch outside diameter aluminum tubing is the preferred material to use as the heat exchanger. Such material is easily formed and sterilized, is inexpensive, and has good heat exchange properties. However, other suitable materials can alternatively be used.

Defoamer 54 is located interiorly of body 30 below heat exchanger 40. The foaming blood flow which is distributed all over the heat exchanger coil descends from the heat exchanger coil onto defoamer 54. An open cell synthetic polymer composition material such as "Scottfoam," which is coated with silicone, is employed as the defoamer. The surface effect of the silicone separates the entrained gas from the liquid blood so that the gas moves upward and can be vented. Vent 56 is an opening in the cover of dome 28 for the addition of fluids and medications. Gap 60 is provided at the periphery of dome 28 where it extends down around the top of the main body of the oxygenator.

The vent fitting 58 is provided so that vacuum can be attached to conduct harmful gases away from the oxygenator. Some of the anaesthetic gases used in the operating room are placed in the blood and are vented along with the carbon dioxide into the operating room when no other provision is made. This may harm operating room personnel. (There have been some reported cases of trauma in operating room personnel caused by exposure to such anaesthetic gases.) Vent connector 58 permits the employment of vacuum to withdraw the vented gases out of the operating room. Dome 28 engages over body 30 and seals thereagainst, except the gap 60 is a vent opening which allows the free escape of the waste gases to the atmosphere. This escape is provided for those cases where it is not necessary to vent the gases out of the operating room. When vacuum is used through vent connector 58, free air is sucked into vent opening 60 and thus prevents lowering the pressure within the oxygenator 60 to subatmosphere.

Dome 28 has skirt 62 depending downwardly therefrom. This skirt guides the downwardly flowing blood foam onto the top of defoamer 54, and at the same time, provides an outer passage through which the separated gases can escape. Another circumferential body of defoamer sponge 64 is provided in this annular opening to ensure that no blood foam reaches the chamber 84 or outside of the oxygenator through vent connection 58 or vent opening 60.

Tray 66 supports the lower part of defoamer body 54 and has exterior walls 68 which constrain the sponge around the outer periphery. Tray 66 has feet 99 to rest on reservoir 84 of oxygenator body 30. Gases or blood may pass between upper and lower parts of oxygenator 10. Filter section 72 is part of the tray and is a conical or cylindrical structure 72 having a bottom 74. The filter section 72 has its interior open to the space above tray 66 and may contain defoamer body 76. Filter 80 is a woven filter which presents little resistance to the flow of blood which passes down from the defoamer body 54 interiorly of filter section 72. Alternatively, filter 72 may be a molded homogeneous porous structure. The blood outflowing through filter 80 from filter section 72 is thus subjected to final filtration. Filter 80 is preferably a woven mesh made from blood-compatible synthetic polymer composition material with a preferred porosity between 100 and 250 microns. The filter material is blood-wettable so that, when it is wet with blood, it prevents gaseous bubbles from passing through. This is the final separation of gas from the blood with the gas constrained on the inside of filter section 72. Despite this constraint, the arterial reservoir 82 also has its top open to the vents by the opening between the fit of the tray 66 onto shoulder 70 by means of feet 99.

Arterial reservoir 82 has enlarged large volumes at the top by means of shoulders 108 and 84 and a small volume at the bottom by the tapered body 86 of the arterial reservoir. This shape provides more resolution at the bottom end with a larger storage capacity at the top. The top end widens suddenly by shoulder 84, but this is at a level which is normally above the usual, normal blood level. Thus, should sudden reservoir capacity be required, it is available in a manner which requires little vertical space. Further space is in shoulder 84 until reservoir overflow through vent opening 60.

Outlet pocket 88 is formed on the bottom of tapered body 86 of the reservoir. Outlet fittings 90 and 92 are for connection to outlet tubes 94 and 96. The arterial outlet fitting 92 and its arterial tube line 96 deliver blood to the arterial pump and thence to the patient. Arterial fitting 90 and its tube 94 serve as a coronary perfusion outlet. Anti-vortex plate 98 is positioned over arterial outlet 88 to prevent vortex formation. Blood flow is unobstructed around the edges of the plate. The vortex plate permits the blood level to be drawn considerably lower in arterial reservoir 82 without ingesting air into the arterial outlet line by means of vortexing. The arterial outlet fittings 90 and 92 are directed downward so that outflow is straight downward. This permits the arterial tubing to hang down in a natural arch under the arterial reservoir without kinking.

Sample port 110 has a Luer opening for arterial blood sample-taking. The sample is taken through a tube positioned inside filter 80 and near the bottom of reservoir 82. If air is blown in through arterial sample port 110, the bubbles stay inside filter 80 and do not pass into the main arterial blood reservoir.

In use in the operating room, the heart-lung pump console usually has a vertical support rod 100 secured thereto. Clamp 102 carries an open metal hoop 104 thereon. Hoop 104 fits under shoulder 70 of body 30. Hoop 104 pivots around pin 105 so that the oxygenator can swing to any convenient position. The open gap 106 permits the oxygenator to be removed while the tubing is still attached to it without the necessity of removal or cutting the tubing. This makes removal and cleanup more convenient, yet allows the operator to rotate the oxygenator into the desired position. Thus, the oxygenator 10 is easy to use.

The shape of the oxygenator is such that it can be placed close to the floor when in use, and thus blood can be drained into it more efficiently. Little priming volume is required so that the biological priming fluid or blood used for priming prior to surgery is of smaller volume to result in less cost, weight, and less risk of material contamination. Dynamic holdup is reduced to produce fast response.

Dimple 97 supports the filter structure and can receive an arterial reservoir temperature sensor.

This invention having been described in its preferred embodiment, it is clear that it is susceptible to numerous modifications and embodiments within the ability of those skilled in the art and without the exercise of the inventive faculty. Accordingly, the scope of this invention is defined by the scope of the following claims.

What is claimed is:
1. A blood oxygenator comprising:
   a substantially rigid housing;
   means defining an interior flow path between an upper portion of said housing and a lower portion of said housing;
   blood foaming means carried by said housing and comprising blood and oxygen inlet passageways for providing a flow of oxygen bubbles into venous blood to create a blood foam, said blood foaming means communicating with said flow path in said upper portion of said housing to direct the flow of blood foam thereinto;

said flow path including a substantially horizontal imperforate plate disposed in said upper portion of said housing to receive blood foam from said foaming means in a direction substantially parallel thereto, and a substantially horizontal perforate plate carried in said upper portion of said housing, below said imperforate plate to receive blood foam flowing over the edge thereof, said perforate plate having perforations to permit blood foam to flow downwardly therethrough;

defoaming means carried in said flow path below said perforate plate to separate liquid blood and gas thereby defoaming the blood; and an arterial blood reservoir, including outlet means therefrom, defined in said lower portion of said housing and communicating with said flow path to collect liquid blood from said defoaming means.

2. A blood oxygenator comprising:

a substantially rigid housing including means defining an interior flow path between an upper portion of said housing and a lower reservoir-defining portion of said housing;

blood foaming means comprising blood and oxygen inlet passageways for providing a flow of oxygen bubbles into venous blood to create a blood foam, said blood foaming means communicating with said flow path in said upper portion of said housing to direct the flow of blood foam thereinto;

defoaming means carried in said flow path above said reservoir and below the level at which blood foam communicates therewith to gravitationally receive and separate blood foam into liquid blood and gas, said defoaming means comprising defoaming material spanning said flow path;

vent opening means in said flow path for venting gas separated from the blood foam, said vent opening means being adjacent a lateral edge portion of said defoaming means, whereby gas separated from the blood foam vents generally laterally through said defoaming means; and a support plate spanning said flow path, said support plate having opening means therein and being downwardly inclined toward said opening means, and a generally tubular-shaped filter element depending from said support plate into said reservoir and being in communication with said opening means, said defoaming material spanning said flow path being carried by said support plate.

3. An oxygenator in accordance with claim 2 wherein said support plate rests on an interior shoulder defined by a reduced diameter portion of said housing.

4. An oxygenator in accordance with claim 2 further comprising a plate disposed in said blood reservoir above outlet means from said reservoir for preventing the formation of vortices in said liquid blood.

5. A blood oxygenator comprising:

a substantially rigid body, gas venting passages in said body to vent gas from said body;

a substantially vertical venous blood passage, a tubular cylindrical porous sparger having said venous blood passage extending therethrough, an oxygen chamber around said tubular sparger so that oxygen bubble flow enters the venous blood passage through said sparger to foam the venous blood, a blood foam passage from the top of said sparger to the top of said body;

a generally horizontal heat exchanger comprising a flat wound tubular coil in said body and passage means for delivering blood foam down through said heat exchanger;

a defoamer directly positioned beneath said heat exchanger so that gravitationally delivered downwardly flowing temperature controlled blood foam is delivered to said defoamer and liquid blood and gas are downwardly delivered from said defoamer; and an arterial blood reservoir in said body below said defoamer so that blood from said defoamer gravitates into said arterial blood reservoir.

6. An oxygenator in accordance with claim 5 further comprising a distributor system located above said horizontal heat exchanger, with said blood foam passage delivering foaming blood to said distributor system.

7. A blood oxygenator comprising:

a substantially rigid housing, including means defining an interior flow path between an upper portion of said housing and a lower portion of said housing;

blood foaming means carried by said housing and comprising blood and oxygen inlet passageways for providing a flow of oxygen bubbles into venous blood to create a blood foam, said blood foaming means communicating with said flow path in said upper portion of said housing to direct the flow of blood foam thereinto;

said flow path including a substantially horizontal imperforate plate disposed in said upper portion of said housing to receive blood foam thereonto from said foaming means, and a substantially horizontal perforate plate carried in said upper portion of said housing below said imperforate plate to receive blood foam flowing over the edge thereof, said perforate plate having perforations to permit blood foam to flow downwardly therethrough;

heat exchanger means carried in said flow path below said perforate plate to control the temperature of blood foam as it moves along said flow path;

defoaming means carried in said flow path below said heat exchanger means to receive blood foam from said heat exchanger means and to separate liquid blood and gas thereby defoaming the blood; and an arterial blood reservoir, including outlet means therefrom, defined in said lower portion of said housing and communicating with said flow path to collect liquid blood from said defoaming means.

8. An oxygenator in accordance with claim 7 wherein said blood foaming means is adapted to direct the flow of blood foam onto said imperforate plate in a direction substantially parallel therewith to provide a spreading of the blood foam thereacross to enhance oxygen transfer.

9. An oxygenator in accordance with claim 7 wherein said imperforate plate is spaced from the top of said housing, said perforate plate is spaced from said imperforate plate and said heat exchanger is spaced from said perforate plate.

10. An oxygenator in accordance with claim 7 wherein said lower portion of said housing is relatively narrower than said upper portion and depends therefrom to define a generally funnel shaped housing to aid in collecting liquid blood in said reservoir in said lower portion.

11. An oxygenator in accordance with claim 7 further comprising a plate disposed in said blood reservoir above said outlet means for preventing the formation of vortices in said liquid blood.

12. An oxygenator in accordance with claim 7 wherein said blood foaming means comprises a tubular porous sparger with said blood passageway extending therethrough and said oxygen inlet passageway communicating with the exterior of said sparger, whereby said sparger generates a flow of oxygen bubbles into the venous blood to create blood foam.

13. An oxygenator in accordance with claim 12 wherein said sparger is made of hydrophobic material and includes an oxygen filter on the exterior surface thereof.

14. An oxygenator in accordance with claim 7 wherein said blood inlet passageway and said reservoir outlet means each comprises a downwardly directed connector for attachment to connective tubing extending between the oxygenator and a patient.

15. An oxygenator in accordance with claim 14 further comprising a length of generally flexible tubing attached to one of said connectors and hanging in a half loop to prevent escape of gas to a patient.

16. An oxygenator in accordance with claim 7 further comprising a support plate carried within said housing and supporting said horizontal portion of said defoaming means, a plate having center opening means and being downwardly inclined toward said center opening means, to direct liquid blood therethrough, and a generally tubular filter element depending from said support plate and communicating with said center opening means to receive and filter liquid blood before it exits the housing.

17. An oxygenator in accordance with claim 16 wherein at least a portion of said defoaming means is also carried within said tubular filter element.

18. An oxygenator in accordance with claim 7 wherein said heat exchanger means comprises a continuous horizontally disposed tubular heat exchanger substantially spanning said flow path.

19. An oxygenator in accordance with claim 18 wherein the ends of said heat exchanger extend through said housing above the blood foaming level in said housing.

20. An oxygenator in accordance with claim 18 in which said tubular heat exchanger comprises a flat wound coil and said flow path comprises a wall interiorly of and a wall exteriorly of said coil to constrain downwardly flowing blood foam to flow through said coil.

21. A blood oxygenator comprising:
a substantially rigid, generally funnel-shaped housing having a defined upper portion providing a blood oxygenating, temperature controlling and defoaming region and a narrower lower portion depending from said upper portion and providing an interior liquid blood reservoir, including outlet means therefrom;
means defining an interior flow path between said upper portion of said housing and said lower portion of said housing;
blood foaming means carried by said housing and comprising blood and oxygen inlet passageways for providing a flow of oxygen bubbles into the blood to create a blood foam, said blood foaming means communicating with said flow path in said upper portion of said housing to direct the flow of blood foam thereinto;
heat exchanger means disposed in said flow path in the upper portion of said housing, below the level at which blood foam communicates therewith to control the temperature of blood as it moves along said flow path;
defoaming means carried in said flow path in said upper portion of said housing downstream of said heat exchanger means to separate liquid blood and gas, thereby defoaming the blood, and
whereby said funnel-shaped housing comprises at least a portion of said means defining an interior flow path to aid in directing the flow of blood into said reservoir.

22. An oxygenator in accordance with claim 21 wherein said blood inlet passageway and said reservoir outlet means each comprises a downwardly directed connector for attachment to connective tubing extending between the oxygenator and a patient.

23. An oxygenator in accordance with claim 22 further comprising a length of generally flexible tubing attached to one of said connectors and hanging in a half loop to prevent escape of gas to a patient.

24. An oxygenator in accordance with claim 21 further comprising a plate disposed in said blood reservoir above said outlet means for preventing the formation of vortices in said liquid blood.

25. An oxygenator in accordance with claim 21 wherein said blood foaming means comprises a tubular porous sparger with said blood passageway extending therethrough and said oxygen inlet passageway communicating with the exterior of said sparger, whereby said sparger generates a flow of oxygen bubbles into the venous blood to create blood foam.

26. An oxygenator in accordance with claim 25 wherein said sparger is made of hydrophobic material and includes an oxygen filter on the exterior surface thereof.

27. An oxygenator in accordance with claim 21 further comprising a support plate carried within said housing and supporting at least a portion of said defoaming means, said plate having center opening means and being downwardly inclined toward said center opening means to direct liquid blood therethrough, and a generally tubular filter element depending from said support plate and communicating with said center opening means to receive and filter liquid blood before it exits the housing.

28. An oxygenator in accordance with claim 27 wherein at least a portion of said defoaming means is also carried within said tubular filter element.

29. An oxygenator in accordance with claim 21, said flow path further comprising a substantially flat imperforate distributor plate horizontally positioned in said relatively large upper portion of said housing, said blood foaming means being adapted to direct the flow of blood foam onto said imperforate plate in a direction substantially parallel therewith to provide a spreading of the blood foam thereacross to enhance oxygen transfer.

30. An oxygenator in accordance with claim 29 further comprising a perforate distributor plate between said imperforate plate and said heat exchanger means, to receive blood foam flowing over the edge of said imperforate plate and having perforations disposed to distribute the blood foam therethrough substantially evenly to said heat exchanger means.

31. An oxygenator in accordance with claim 30 wherein said imperforate plate is spaced from the top of said housing, said perforate plate is spaced from said imperforate plate and said heat exchanger means is spaced from said perforate plate.

32. An oxygenator in accordance with claim 29 wherein said heat exchanger means comprises a continuous horizontally disposed tubular heat exchanger substantially spanning said flow path.

33. An oxygenator in accordance with claim 32 wherein the ends of said heat exchanger extend through said housing above the blood foaming level in said housing.

34. An oxygenator in accordance with claim 32 in which said tubular heat exchanger comprises a flat wound coil and said flow path comprises a wall interiorly of and a wall exteriorly of said coil to constrain downwardly flowing blood foam to flow through said coil.

35. A blood oxygenator comprising:
a substantially rigid housing including means defining an interior flow path between an upper portion of said housing and a lower reservoir-defining portion of said housing;
blood foaming means comprising blood and oxygen inlet passageways for providing a flow of oxygen bubbles into venous blood to create a blood foam, said blood foaming means communicating with said flow path in said upper portion of said housing to direct the flow of blood foam thereinto;
defoaming means carried in said flow path above said reservoir and below the level at which blood foam communicates therewith to gravitationally receive and separate blood foam into liquid blood and gas, said defoaming means comprising defoaming material substantially horizontally spanning said flow path;
vent opening means in said flow path for venting gas separated from the blood foam, said vent opening means being adjacent a lateral edge portion of said defoaming means, whereby gas separated from the blood foam vents generally laterally through said defoaming means; and
heat exchanger means in said flow path downstream of said foaming means and upstream of said defoaming means to regulate the temperature of blood foam moving therealong.

36. An oxygenator in accordance with claim 35 wherein said heat exchanger means comprises a continuous horizontally disposed tubular heat exchanger substantially spanning said flow path.

37. An oxygenator in accordance with claim 36 wherein the ends of said heat exchanger extend through said housing above the blood foaming level in said housing.

38. An oxygenator in accordance with claim 36 in which said tubular heat exchanger comprises a flat wound coil and said flow path comprises a wall interiorly of and a wall exteriorly of said coil to constrain downwardly flowing blood foam to flow through said coil.

39. An oxygenator in accordance with claim 35, said flow path further comprising distributor means above said heat exchanger means for enhancing oxygen transfer to the venous blood and for distributing blood foam evenly to said heat exchanger means, said distributor means comprising a substantially flat, imperforate distributor plate to receive blood foam from said blood foaming means and a perforated distributor plate therebelow to receive blood foam flowing over the edge of said imperforate plate, said perforated plate having perforations disposed to distribute blood foam, therethrough substantially evenly to said heat exchanger means therebeneath.

40. An oxygenator in accordance with claim 39 wherein said imperforate and perforate distributor plates are substantially horizontal, said blood foaming means being adapted to direct the flow of blood foam onto said imperforate plate in a direction substantially parallel therewith to provide a spreading of the blood foam thereacross to enhance oxygen transfer.

41. An oxygenator in accordance with claim 39 wherein said imperforate plate is spaced from the top of said housing, said perforate plate is spaced from said imperforate plate and said heat exchanger is spaced from said perforate plate.

42. A blood oxygenator comprising:
a generally funnel-shaped housing, including an upper portion and a narrower lower portion defining a liquid blood reservoir therewithin, and including outlet means from said reservoir;
means defining an interior flow path between said upper and lower housing portions;
blood foaming means comprising venous blood and oxygen inlet passageways for providing a flow of oxygen bubbles into venous blood to create a blood foam, said blood foaming means communicating with said flow path in said upper portion of said housing to direct the flow of blood foam thereinto;
horizontally disposed heat exchanger means carried in said flow path in said upper portion of said housing below the level at which said blood foam communicates therewith to control the temperature of blood foam as it flows downwardly through said housing;
defoaming means carried in said flow path below said heat exchanger means to receive heated blood foam therefrom to separate liquid blood and gas, said defoaming means comprising a horizontal portion underlying and substantially spanning said heat exchanger means in said upper portion of said housing, and a vertically disposed portion below said horizontal portion and extending into the narrower lower blood reservoir of said housing to conduct the flow of liquid blood thereinto.

43. An oxygenator in accordance with claim 42 further comprising a support plate carried within said housing and supporting said horizontal portion of said defoaming means, said plate having center opening means and being downwardly inclined toward said center opening means to direct liquid blood therethrough, and a generally tubular filter element depending from said support plate and communicating with said center opening means to receive and filter liquid blood before it exits the housing, said vertically disposed defoamer portion extending substantially into said filter element.

44. An oxygenator in accordance with claim 42 further comprising a plate disposed in said blood reservoir above said outlet means for preventing the formation of vortices in said liquid blood.

45. An oxygenator in accordance with claim 42 wherein said blood foaming means comprises a tubular porous sparger with said blood passageway extending therethrough and said oxygen inlet passageway communicating with the exterior of said sparger, whereby said sparger generates a flow of oxygen bubbles into the venous blood to create blood foam.

46. An oxygenator in accordance wih claim 45 wherein said sparger is made of hydrophobic material and includes an oxygen filter on the exterior surface thereof.

47. An oxygenator in accordance with claim 42 in which said tubular heat exchanger comprises a flat wound coil and said flow path comprises a wall interiorly of and a wall exteriorly of said coil to constrain downwardly flowing blood foam to flow through said coil.

48. An oxygenator in accordance with claim 47 wherein the ends of said heat exchanger extend through said housing above the blood foaming level in said housing.

49. An oxygenator in accordance with claim 42 wherein said blood inlet passageway and said reservoir outlet means each comprises a downwardly directed connector for attachment to connective tubing extending between the oxygenator and a patient.

50. An oxygenator in accordance with claim 49 further comprising a length of generally flexible tubing attached to one of said connectors and hanging in a half loop to prevent escape of gas to a patient.

51. An oxygenator in accordance with claim 42, said flow path further comprising distributor means above said heat exchanger means for enhancing oxygen transfer to the venous blood and for distributing blood foam evenly to said heat exchanger means, said distributor means comprising a substantially flat, imperforate distributor plate to receive blood foam from said blood foaming means and a perforated distributor plate therebelow to receive blood foam flowing over the edge of said imperforate plate, said perforated plate having perforations disposed to distribute blood foam, therethrough substantially evenly to said heat exchanger means therebeneath.

52. An oxygenator in accordance with claim 51 wherein said imperforate and perforate distributor plates are substantially horizontal, said blood foaming means being adapted to direct the flow of blood foam onto said imperforate plate in a direction substantially parallel therewith to provide a spreading of the blood foam thereacross to enhance oxygen transfer.

53. An oxygenator in accordance with claim 52 wherein said imperforate plate is spaced from the top of said housing, said perforate plate is spaced from said imperforate plate and said heat exchanger is spaced from said perforate plate.

54. A blood oxygenator comprising:
a substantially rigid housing;
means defining an interior flow path between an upper portion of said housing and a lower portion of said housing;
blood foaming means carried by said housing and comprising blood and oxygen inlet passageways for providing a flow of oxygen bubbles into venous blood to create a blood foam, said blood foaming means communicating with said flow path in said upper portion of said housing to direct the flow of blood foam thereinto;
a horizontally disposed continuous tubular heat exchanger substantially spanning said flow path below the level at which blood foam communicates therewith to control the temperature of blood foam as it moves along said flow path, the ends of said heat exchanger extending through said housing above the blood foaming level in said housing;
defoaming means carried in said flow path below said head exchanger to receive blood foam from said heat exchanger and to separate liquid blood and gas thereby defoaming the blood; and
an arterial blood reservoir, including outlet means therefrom, defined in said lower portion of said housing and communicating with said flow path to collect liquid blood from said defoaming means.

55. A blood oxygenator comprising:
a substantially rigid housing;
means defining an interior flow path between an upper portion of said housing and a lower portion of said housing;
blood foaming means carried by said housing and comprising blood and oxygen inlet passageways for providing a flow of oxygen bubbles into venous blood to create a blood foam, sad blood foaming means communicating with said flow path in said upper portion of said housing to direct the flow of blood foam thereinto;
a tubular heat exchanger carried in said flow path below the level at which blood foam communicates therewith to control the temperature of blood foam as it moves along said flow path, said heat exchanger comprising a flat wound coil and said flow path comprising a wall interiorly of and a wall exteriorly of, said coil to constrain downwardly flowing blood foam to flow through said coil;
defoaming means carried in said flow path below said heat exchanger to receive blood foam from said heat exchanger and to separate liquid blood and gas thereby defoaming the blood; and
an arterial blood reservoir, including outlet means therefrom, defined in said lower portion of said housing and communicating with said flow path to collect liquid blood from said defoaming means.

56. A blood oxygenator comprising;
a substantially rigid housing;
means defining an interior flow path between an upper portion of said housing and a lower portion of said housing;
blood foaming means carried by said housing and comprising blood and oxygen inlet passageways for providing a flow of oxygen bubbles into venous blood to create a blood foam, said blood foaming means communicating with said flow path in said upper portion of said housing to direct the flow of blood foam thereinto;
defoaming means carried in said flow path below the level at which blood foam communicates therewith to gravitationally receive and separate blood foam into liquid blood and gas;
a support plate carried within said housing and supporting said defoaming means, said plate having center opening means and being downwardly inclined toward said center opening means to direct liquid blood therethrough, and a generally tubular filter element depending from said support plate and communicating with said center opening means to receive and filter liquid blood; and
an arterial blood reservoir, including outlet means therefrom, defined in said lower portion of said housing and communicating with said flow path to collect liquid blood.

57. An oxygenator in accordance with claim 56, wherein at least a portion of said defoaming means is disposed within said tubular filter element.

58. An oxygenator in accordance with claim 56 wherein said support plate rests on an interior shoulder defined by a reduced diameter portion of said housing.

* * * * *